United States Patent [19]

Gallop et al.

[11] 4,267,295

[45] May 12, 1981

[54] POLYMERIC COMPOSITIONS AND HYDROGELS FORMED THEREFROM

[75] Inventors: Paul M. Gallop, Chestnut Hill; Donald R. Korb, Boston, both of Mass.

[73] Assignee: Syntex (U.S.A.) Inc., Palo Alto, Calif.

[21] Appl. No.: 10,992

[22] Filed: Feb. 9, 1979

[51] Int. Cl.³ .................................................. C08F 220/20
[52] U.S. Cl. ........................................ 526/264; 526/320; 433/167; 128/1 R; 260/29.6 TA; 351/160 H; 424/81; 526/273; 526/287; 526/301; 526/303; 526/304; 526/311; 526/317; 526/318
[58] Field of Search ............... 526/264, 273, 287, 303, 526/301, 304, 311, 317, 318, 320

[56] References Cited

U.S. PATENT DOCUMENTS 3,957,362   5/1976   Mancini et al. ........................ 526/320
4,056,496  11/1977   Mancini et al. ........................ 526/320

*Primary Examiner*—Harry Wong, Jr.
*Attorney, Agent, or Firm*—Howard M. Peters; Joseph I. Hirsch

[57] ABSTRACT

The invention provides new hydrogel forming materials comprising synthetic, hydrophilic, aqueous-insoluble polymer networks formed by copolymerization of a hydrophilic dihydroxyalkyl acrylate or methacrylate, a substantially water insoluble alkyl acrylate or methacrylate, one or more additional hydrophilic comonomers selected from the group of vinylic monomers, acrylates, and methacrylates, and a cross-linking agent. The hydrogels are preferably used for the formation of contact lenses, but may also be used for drug and pesticides delivery devices; dialysis, ultrafiltration and reverse osmosis membranes; implants in surgery and dentistry; and the like.

30 Claims, No Drawings

POLYMERIC COMPOSITIONS AND HYDROGELS FORMED THEREFROM

BACKGROUND OF THE INVENTION

1. Introduction

This invention relates to polymers and hydrogels of polymers formed from alkyl acrylates or methacrylates, dihydroxyalkyl acrylates or methacrylates, a third comonomer selected from those hereinafter described, and a cross-linking agent. The polymers absorb water to form hydrogels useful in medical and other applications and are especially useful for the formation of contact lenses.

2. Description of the Prior Art

The synthetic aqueous polymer networks known as hydrogels are three dimensional networks of polymers, generally covalently or ionically cross-linked, which interact with aqueous solutions by swelling to some equilibrium state. That is, a hydrogel is a polymeric material which exhibits the ability to swell in water and retain a significant fraction of the imbibed water within its structure. Absent such imbibed water, these materials are properly termed xerogels.

These materials have growing application in the medical field based on their bulk and surface properties. They are especially of interest for their resemblance to living tissue, for example, in their physical properties of high water content and soft, rubbery consistency.

Hydrogel materials are described in U.S. Pat. Nos. 2,976,576 and 3,220,960 incorporated herein by reference. These materials, intended for use as contact lens materials, are hydrogels of a sparingly cross linked hydrophilic copolymer and a substantial quantity of an aqueous liquid, e.g. water. The hydrophilic polymer is a copolymer of a major amount of a polymerizable monoester of an olefinic acid selected from the group of acrylic and methacrylic acids having a single olefinic double bond and a minor amount of a polymerizable diester of one of said acids, the diester having at least two olefinic double bonds. The copolymer is formed by copolymerization in a solvent medium.

Copolymers that are solvent soluble, but water insoluble formed from gylceryl methacrylate and methyl methacrylate are known and described by H. Yasuda, C. E. Lamaza, and L. D. Ikenberry, *Makromol. Chem.* 118, 1935 (1968) and H. Yasuda, C. E. Lamaza, and A. Peterlin, *J. Polym. Sc.* Part A-2, 996, 1117–1131 (1971).

In U.S. Pat. No. 4,056,496, incorporated herein by reference, hydrogels are disclosed which are suitable for soft lens fabrication. The hydrogels are formed from a hydrophilic monomer from the group of dihydroxyalkyl acrylates and methacrylates, a substantially water insoluble monomer from the group of alkyl acrylates and methacrylates and preferably a minor amount of an epoxidized alkyl acrylate or methacrylate. The dihydroxyalkyl acrylate is preferably used in major amount, the alkyl acrylate in minor amount, and the epoxidized acrylate in an amount sufficient to impart the desired rigidity. The polymer is formed by a free radical, bulk polymerization process in the substantial absence of solvent. The materials thus formed are useful after hydration as soft contact lens material.

Due to the rapidly expanding areas of application of hydrogel materials, new such materials providing improved and/or different physical properties are greatly sought after. One particular area of improvement is in the fraction of aqueous solution which can be retained by the hydrogel within its structure. Typically, the higher the water content of the hydrogel, the poorer the mechanical properties thereof. Nevertheless, higher water content is often desirable, such as for medical applications where high water content is believed to be a major factor in the biocompatibility of the hydrogel. Of course, water insolubility is essential for most medical application. Accordingly, new materials are sought which will retain a greater fraction of aqueous solution within their structure while having comparable or even improved mechanical properties.

SUMMARY OF THE INVENTION

The present invention provides a class of new hydrogel forming polymers suitable for medical and other applications, such as the formation of contact lenses, comprising a copolymer of an hydrophilic monomer selected from the group of dihydroxyalkyl acrylate and methacrylates (hereinafter collectively termed "dihydroxyalkyl acrylates"), a substantially water insoluble monomer selected from the group of alkyl acrylates and methacrylates (hereinafter collectively termed "alkyl acrylates"), one or more additional monomers selected from the group of vinylic monomers, and hydrophilic acrylates and methacrylates as further described herein, and a crosslinking agent in sufficient quantity to provide the desired mechanical properties.

DETAILED DESCRIPTION OF THE INVENTION AND PREFERRED EMBODIMENTS

Any hydrophilic dihydroxyalkyl acrylate monomer can be used in the practice of this invention. Particularly useful, such monomers are those having the following general formula:

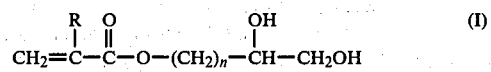

$$CH_2=\overset{R}{\underset{|}{C}}-\overset{O}{\underset{\|}{C}}-O-(CH_2)_n-\overset{OH}{\underset{|}{CH}}-CH_2OH \qquad (I)$$

where R is hydrogen or methyl and n is a whole integer having a value of from one to four, preferably one or two. Examples of such dihydroxyalkyl acrylates include dihydroxypropyl methacrylates; dihydroxybutyl methacrylates; dihydroxypentyl methacrylates; dihydroxyhexyl methacrylates; dihydroxypropyl acrylates; dihydroxybutyl acrylates; dihydroxypentyl acrylates; dihydroxyhexyl acrylates; and the like. A preferred dihydroxyalkyl acrylate is 2,3-dihydroxypropyl methacrylate (glyceryl methacrylate).

The dihydroxyalkyl acrylate can be formed by hydrolysis following the procedures set forth in British Pat. No. 852,384, incorporated herein by reference. The preferred 2,3-dihydroxypropyl methacrylate may be made by the process disclosed therein, but is preferably prepared in accordance with the process described by M. F. Refojo, *Journal of Applied Polymer Science*, Volume 9, pp. 3161–3170 (1965). This process involves the hydrolysis of glycidyl methacrylate and solvent extraction from the reaction mixture subsequent to the hydrolysis reaction as illustrated below.

EXAMPLE 1

One hundred grams of commercial glycidyl methacrylate (American Aniline and Extract Company, Inc.-GMA), 150 ml distilled water and 0.25 ml of concentrated sulfuric acid were stirred for six days. During the experiment, the reaction flask was kept in a water bath at 24°-29° C. No additional inhibiting agent was added to the reaction mixture other than the amount present in the commercial gylcidyl methacrylate.

Glycidyl methacrylate is immiscible with water, but as the reaction proceeds, solubility is increased until a clear solution is obtained. As the reaction proceeds, glyceryl methacrylate is formed which co-dissolves the unreacted glycidyl methacrylate.

The reaction mixture was neutralized with 10% sodium hydroxide and then extracted with five 100 ml portions of ether. The ether extract was washed with three 20 ml portions of distilled water, then this aqueous solution was washed again with 50 ml of ether. The combined ether extracts were dried with anhydrous sodium sulfate. The ether was then evaporated in a rotating evaporator with the rotating flask kept in a cool water bath. The residue from the ether extract, 18.8 g, was mainly glycidyl methacrylate which could be used to prepare more glyceryl methacrylate.

The aqueous extract from the ether solution was saturatedd with sodium chloride. The glyceryl methacrylate separated out as an oily layer above the saturated saline solution. The oily material was dissolved in methylene chloride. The organic solution was dried with anhydrous sodium sulfate and evaporated, without heating, but using the same procedure described above for the concentration of the ether extract. The residue from the evaporation (11.6 g) was a viscous, clear liquid, namely glyceryl methacrylate.

The aqueous reaction medium, previously extracted with ether, upon saturation with sodium chloride, separated into two layers. The organic layer was taken up with methylene chloride and the solution, after being dried with anhydrous sodium sulfate, was evaporated in the rotating evaporator by using a cool water bath under the rotating flask. The yield was 71.6 g of glyceryl methacrylate. This reaction product also contained between about 1.8% and 2.2% by weight of unreacted glycidyl methacrylate which was not removed in the extraction step. Minor amounts of other impurities, such as methacrylic acid, glyceryl methacrylate diester and/or glyceryl methacrylate triester, may also have been present.

Other dihydroxyalkyl acrylates can be made in a similar manner.

The second monomer can be any substantially water insoluble alkyl acrylate or alkyl methacrylate. Particularly useful such monomers are those having the general formula:

$$CH_2=C(R')-C(O)-OR^2 \quad (II)$$

where R' is hydrogen or methyl and $R^2$ is an alkyl group preferably having from about 1 to 6 carbon atoms. Alkyl acrylates conforming to this formula are readily available. Examples of suitable such acrylates include methyl acrylate, methylmethacrylate, ethyl acrylate, ethyl methacrylate, propyl acrylate, propyl methacrylate, isopropyl acrylate, isopropyl methacrylate, butyl methacrylate, and the like, etc. Methyl methacrylate is presently preferred.

The third monomer comprises one or more of the following:

(A) A vinylic monomer conforming to the formula:

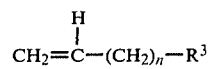

where $R^3$ is a hydrophilic moiety comprising, for example, hydroxyl; alkoxy, preferably having 1 to 6 carbon atoms and more preferably methoxy or ethoxy; an acidic group, such as sulfonic acid moiety;

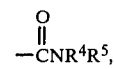

wherein $R^4$ and $R^5$ are independently selected from a hydrogen atom and alkyl or substituted alkyl groups having from 1 to about 3 carbon atoms, and $R^4$ and $R^5$ may be combined to form a cyclic group; or

wherein $R^4$ and $R^5$ are defined as above and may be combined to form a lactam such as pyrrolidone or piperidone; and n is zero to four, except that when $R^3$ is hydroxyl, n must be at least one. Examples of suitable vinylic comonomers include vinyl acetate, 3-buten-1-ol, 2-propen-1-ol, 5-hexenol, methyl vinyl ether, propyl vinyl ether, butyl 3-buten-1-ol ether, N-methyl vinyl amide, N-propyl vinyl amide, N-ethyl-3-butenamide. A preferred monomer is vinyl pyrrolidone,

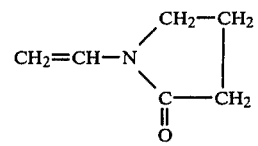

(B) Hydrophilic acrylates having the formula:

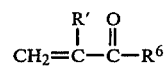

where $R^6$ is amido, hydroxyalkoxy, preferably having 1 to 6 carbon atoms, or other hydrophilic group and R' is hydrogren or methyl as above. Examples of such acrylates include, for instance, 3-hydroxypropyl acrylate, 2-hydroxyethyl methacrylate, methacrylamide, N-methyl methacrylate, N,N-dimethyl methacrylamide, and the like, etc. Preferred third monomers include 2-hydroxyethyl acrylate,

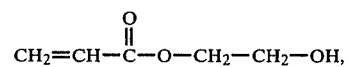

and the acrylamides

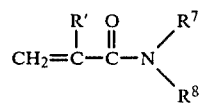

where $R^7$ and $R^8$ are independently selected from hydrogen or lower alkyl groups, particularly alkyl groups having 1 to 4 carbon atoms.

(C) Mixtures of monomers described in paragraphs (A) and (B) above.

It will be noted that a common denominator among the three monomers is the presence in each of an activated carbon-carbon double bond, the site at which polymerization occurs. A significant shared property, however, is the general ability of the monomers to introduce one or more hydrophilic groups to the polymer network to produce an improved hydrogel.

The molar ratio of the dihydroxyalkyl acrylate to the alkyl acrylate can vary within broad limits dependent upon the use to which the material is to be put. Preferably, the ratio varies within the range of from about 1:3 to about 20:1. Preferably, the dihydroxyalkyl acrylate at least equals or exceeds the alkyl acrylate and a preferred ratio varies between about 1:1 and 10:1. More preferably, the molar ratio is about 1.2:1.0 and about 2:1. (For use of the hydrogel as a contact lens material, the most preferred molar ratio is about 1.5:1.0.)

The molar ratio of the third monomer to the total of dihydroxyalkyl acrylate plus alkyl acrylate monomers can also vary within broad limits again dependent upon the use to which the material is to be put. Preferably, the ratio varies within the range of 1:1 down to a negligible amount of third monomer. The most preferred amount of third monomer used will depend both on the particular monomer selected for use and on the mechanical properties most advantageous to the particular application and can be readily determined through a routine series of polymerizations over a range of mole ratios.

The cross-linking agent can by any compound having two reactive olefinic double bonds. Particularly useful compounds for cross-linking in this invention are the divinyl compounds. The cross-linking agent, among other things, aids in providing desirable mechanical properties to the hydrophilic polymers of this invention and enables them to be insoluble in aqueous solutions while imbibing large amounts of such solutions.

As aforesaid, divinyl compounds are particularly useful as cross-linking agents in the practice of this invention. Preferred divinyl compounds include those compounds having diesters with acrylic or methacrylic acid. Typical examples of such preferred compounds include the glycol diesters such as, for instance, ethylene glycol dimethyacrylate, propylene glycol dimethacrylate, ethylene glycol diacrylate, and the like. Other examples of useful cross-linking agents include triethanolamine dimethacrylate, triethanolamine trimethacrylate, tartaric acid dimethacrylate, triethylene glycol dimethacrylate, the dimethacrylate of bishydroxyethylacetamide, and the like.

The amount of such cross-linking agent is dependent upon obtaining the desired rigidity. In general, the concentration does not exceed 5% of the total monomer constituents, preferably ranges between about 0. 1 to 4% and should be in an amount sufficient to yield a hydrogel from the polymer having the desired hydration properties. Desirably, the amount of cross-linking agent is that necessary to provide a polymer capable of absorbing water of hydration in an amount of from about 35 to about 50% by weight and preferably from about 40 to about 46%.

It is believed that epoxidized acrylate acts as a cross-linking agent and may be added in an amount which varies within broad parameters as discussed above. Normally an appreciable amount of unreacted epoxy alkyl ester will remain in the reaction mixture of Example 1 even after repeated solvent extraction steps. This is apparently due to the dihydroxyalkyl acrylate acting as a cosolvent for the ester in the aqueous phase. However, if the amount of unreacted ester present in the dihydroxyalkyl acrylate product is different from the amount necessary in order to get the desired degree of cross-linking, it can be adjusted by addition of epoxy alkyl ester to increase cross-linking or by reducing the amount of ester in the product in order to decrease cross-linking. The amount of ester can be reduced, for example, by further solvent extraction steps, as is well known in the art. Generally, the epoxidized acrylate may be added in an amount of from 0 to 30% by weight of the dihydroxy acrylate monomer, but more preferably, from 0.1 to 15% by weight and most preferably 1.0 to 7.5%, depending upon the particular monomers used, their ratio and other factors.

As to the degree of cross-linking of the gels from the polymers described herein, a guide to the extent of cross-linking is the solubility properties of the gels in various organic solvents. In general, the gels are insoluble in solvents such as dioxane, acetone, methylene chloride and mixtures thereof.

For use as a contact lens, the hydrogels preferably have certain properties. The percent hydration with water has been discussed above. Another property is the percent linear elongation. Preferably, the hydrated gel will exhibit a linear expansion of from about 15 to about 25% and more preferably, from about 18 to about 21%. A further property is the hardness of the material. Preferably, it has a Shore A durometer Type A-2 reading (ASTM Designation D2240-68) of from about 40 to about 50 and more preferably, from about 42 to about 47.

The polymers are generally formed by bulk polymerization using suitable catalysts. The monomers are mixed in the absence of solvent and maintained under reduced pressure at an elevated temperature for a period of time sufficient to solidify the reaction mixture. Typically, the temperature of reaction varies between 20° and 60° C. The catalyst concentration may vary within broad limits dependent upon the particular catalyst used, but generally varies between about 0.0001 and 0.2 weight percent of the hydroxyalkylacrylate, and preferably between 0.0005 and 0.01 weight percent. A wide variety of catalysts are known to initiate the polymerization reaction and one skilled in the art can select any of the known catalysts that are suitable for the particular polymerization being conducted. Preferred catalysts are oxidants such as isopropyl percarbonate and free radical initiators such as azobisisobutyronitrile.

While the uses, medical or otherwise, to which the polymers described herein may eventually be put is impossible to predict, their ability to retain greater amounts of imbibed aqueous solution while having good mechanical properties represents a significant advance in the technology of hydrogels.

Having above generally described the invention, the following examples will illustrate specific embodiments.

EXAMPLE 2

The bulk copolymerization of 2,3-dihydroxypropyl methacrylate (GMA) made in accord with Example 1 with methyl methacrylate (MMA) and vinyl pyrrolidone was carried out. The amount of 1.14 g of said GMA and 0.27 g of vinyl pyrrolidone and 0.27 g of MMA were mixed together. To the mixture was added 1.0 mg of azobisisobutyronitrile as a catalyst. The composition was heated at 80° C. A clear copolymer formed in 10 minutes.

EXAMPLE 3

The bulk copolymerization of GMA made in accord with Example 1 with MMA and methacrylamide was carried out. The amount of 0.5 g MMA and 1.14 g of said GMA and 0.5 g of methacrylamide were mixed and warmed briefly to solution. To the mixture was added 1.0 mg of azobisisobutyronitrile as catalyst. The mixture was heated at 80° C. and a clear copolymer formed within five minutes.

As noted above, the hydrogels of this invention have properties which make them excellent materials for soft contact lens application. After absorbing water (pysiological saline water or water containing a physiologically active solute such as a bacteriostatic agent) the hydrogels are soft and flexible, but at the same time, they are tough and resist tearing. They are somewhat more rigid than prior art materials used for hydrogel contact lenses and consequently, maintain the contour of the eye to a greater extent than prior art materials and may be fabricated in thinner cross section. Moreover, the increased rigidity prevents misshaping by blinking thus preventing an everchanging optical surface with resulting invariations and distortions of vision.

In addition to the above utility of the copolymers of this invention, the physiochemical properties make them suitable for prolonged contact with living tissue, blood and mucous membrane such as would be required for surgical implants, blood dialysis devices and the like. In this respect, it is known that blood, for example, is rapidly damaged when in contact with most artificial surfaces. The design of a synthetic surface which is antithrombogenic and nonhemolytic to blood is necessary for any prosthesis end device to be used with blood. The non-ionic hydrogels, such as those of the subject invention, are known to substantially reduce the clotting tendency of blood.

The hydrogels are also selectively permeable to water and thus, they qualify for various applications involving dialysis, ultrafiltration, and reverse osmosis. In this respect, it is particularly advantageous that the permeability of these hydrogels may be adapted for any desired purpose and the size and shape of a diaphragm may be prepared in situ to form an integral part of a hydrophilic article or device. The good chemical stability of the hydrogels also make them suitable for electrolytic purposes.

The copolymers of the subject invention can also be impregnated with a drug. Then, when the copolymer, in the form of an article made therefrom such as an intrauterine device is administered to a patient, the drug will gradually be released to the patient. As the drug is removed from the surface of the coplymer, it will be replaced with a fresh supply of drug migrating to the surface of the copolymer from its interior.

In a similar manner, the copolymers may be used for controlled release of pesticides. Pesticides, particularly biodegradable pesticides, released gradually by diffusion from the copolymer, when applied in this manner, will reduce environmental hazards associated with the continued usage of conventional pesticides.

The entire article prepared according to this invention forms a lattice of giant swollen molecules when immersed in water. It is therefore not only permeable to water and to certain aqueous solutions, but also strong, of stable shape and very elastic. It can be boiled in water without being damaged whereby thorough sterilization may be achieved. These properties make an article formed from the copolymer of the invention particularly suitable for purposes in surgery, where a body compatible with living tissue or with a mucuous membrane may be used, e.g.- for making contact lenses as described above, for filling or dividing cavities in tissue, for pessaries, etc.

While the present invention has been described in detail along with the preferred embodiments thereof, it is understood that those skilled in the art may effect various modifications within the spirit and scope of this invention.

We claim:

1. A hydrophilic polymer comprising the polymerization product of:

a first monomer comprising a dihydroxyalkyl acrylate, a second monomer comprising a substantially water insoluble alkyl acrylate or alkyl methacrylate, the mole ratio of said first monomer to said second monomer varying within the range from about 1:3 to about 20:1;

a third monomer comprising a compound selected from the group consisting of:

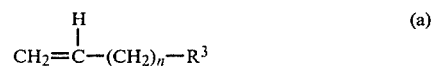  (a)

where $R^3$ is hydroxyl, alkoxy having 1 to 6 carbon atoms, a sulfonic acid moiety,

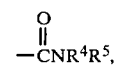, wherein $R^4$ and $R^5$ are independently selected from hydrogen and an unsubstituted or substituted alkyl group having from 1 to about 3 carbon atoms, and $R^4$ and $R^5$ may be combined to form a cyclic group, or

wherein $R^4$ and $R^5$ are as defined above, and n is an integer from 0 to about 4, except that n must be at least 1 when $R^3$ is hydroxyl;

  (b)

where $R^6$ is hydroxyalkoxy having 1 to 6 carbon atoms or $-NR^7R^8$ where $R^7$ and $R^8$ are independently selected from hydrogen and lower alkyl groups having 1 to 4 carbon atoms;

  (c)

where $R^9$ is hyroxyalkoxy having from 1 to about 6 carbon atoms; and (d) mixtures thereof:
the total of the molar quantities of said first and second monmers to the molar quantity of said third monomer being in the range of 1:1 to 1:0.2.

2. The hydrophilic polymer of claim 1 wherein said polymer has a Shore A durometer Type A-2 reading of from about 40 to about 50.

3. The hydrophilic polymer of claim 1 wherein said polymer is insoluble in a solvent selected from the group of acetone, dioxane, or mixtures thereof.

4. The hydrophilic polymer of claim 1 wherein said first monomer comprises a compound having the formula:

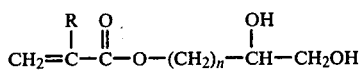

$$CH_2=C-C-O-(CH_2)_n-CH-CH_2OH$$
with R, O, OH groups as shown wherein R is hydrogen or methyl and n is an integer from 1 to 4.

5. The hydrophilic polymer of claim 4 wherein said first monomer comprises a compound selected from the group consisting of dihydroxypropyl methacrylate; dihydroxybutyl methacrylate; dihydroxypentyl methacrylate; dihydroxyhexyl methacrylate; dihydroxypropyl acrylate; dihydroxybutyl acrylate; dihydroxypentyl acrylate; and dihydroxyhexyl acrylate.

6. The hydrophilic polymer of claim 1 wherein said second monomer comprises a compound having the formula:

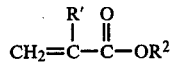

wherein R' is hydrogen or methyl and R² is an alkyl group having from 1 to about 6 carbon atoms.

7. The hydrophilic polymer of claim 6 wherein said second monomer comprises a compound selected from the group consisting of methyl acrylate, methylmethacrylate, ethyl acrylate, ethyl methacrylate, propyl acrylate, propyl methacrylate, isopropyl acrylate, isopropyl methacrylate, and butyl methacrylate.

8. The hydrophilic polymer of claim 1 wherein said third monomer is selected from the group consisting of vinyl acetate 3-buten-1-ol, 2-propen-1-ol, 5-hexenol, methyl vinyl ether, propyl vinyl ether, butyl 3-buten-1-ol ether, N-methyl vinyl amide, N-propyl vinyl amide, N-ethyl-3-butenamide and vinyl pyrrolidone.

9. The hydrophilic polymer of claim 1 wherein said third monomer comprises a compound selected from the group consisting of 3-hydroxypropyl acrylate, 2-hydroxyethyl methacrylate, methacrylamide, N-methyl methacrylamide, N,N-dimethyl methacrylamide, and 2-hydroxyethyl acrylate.

10. A shaped article made from the hydrophilic polymer of any of claims 1 through 5, 6, 7, 8 or 9.

11. The shaped article of claim 10 in the form of a contact lens.

12. The hydrophilic polymer of claim 1 wherein said molar ratio of said first monomer to said second monomer is at least 1:1.

13. The hydrophilic polymer of claim 1 further including a cross-linking agent.

14. The hydrophilic polymer of claim 13 wherein said cross-linking agent comprises a divinyl compound having two reactive olefinic double bonds.

15. The hydrophilic polymer of claim 13 wherein said cross-linking agent is present in an amount less than about 5 mole percent.

16. The hydrophilic polymer of claim 13 wherein said cross-linking agent is selected from the group consisting of ethylene glycol dimethyacrylate, propylene glycol dimethacrylate, ethylene glycol diacrylate, triethanolamine dimethacrylate, triethanolamine trimethacrylate, tartaric acid dimethacrylate, triethylene glycol dimethacrylate, and the dimethacrylate of bishydroxyethylacetamide.

17. The hydrophilic polymer of claim 1 wherein said first monomer comprises a hydrophilic compound having the formula:

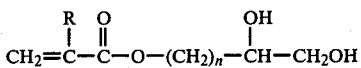

wherein R is hydrogen or methyl and n is an integer from 1 to 4; said second monomer comprises a substantially insoluble acrylate or methacrylate selected from the group consisting of methyl acrylate, methyl methacrylate, ethyl acrylate, ethyl methacrylate, propyl acrylate, propyl methacrylate, isopropyl acrylate, isopropyl methacrylate, butyl acrylate, and butyl methacrylate; and said third monomer is selected from the group consisting of vinyl acetate, 3-buten-1-ol, 2-propen-1-ol, 5-hexenol, methyl vinyl ether, propyl vinyl ether, butyl 3-buten-1-ol ether, N-methyl vinyl amide, N-propyl vinyl amide, N-ethyl-3-butenamide, vinyl pyrrolidone, 3-hydroxypropyl acrylate, 2-hydroxyethyl acrylate, 2-hydroxyethyl methacrylate, methacrylamide, N-methyl methacrylamide, N-N-dimethyl methacrylamide, and mixtures thereof.

18. The hydrophilic polymer of claim 17 wherein said first monomer comprises 2,3-dihydroxypropyl methacrylate.

19. The hydrophilic polymer of claim 17 wherein said second monomer comprises methyl methacrylate.

20. The hydrophilic polymer of claim 17 wherein said third monomer comprises a compound selected from vinyl pyrrolidone, 2-hydroxyethyl acrylate or methacrylamide.

21. The hydrophilic polymer of claim 17 further including a cross-linking agent selected from the group consisting of, ethylene glycol dimethacrylate, propylene glycol dimethacrylate, ethylene glycol diacrylate, triethanolamine dimethacrylate, triethanolamine trimethacrylate, tartaric acid dimethacrylate, triethylene glycol dimethacrylate, and the dimethacrylate of bishydroxyethylacetamide.

22. The hydrophilic polymer of claim 17 wherein said first monomer comprises 2,3-dihydroxypropyl methacrylate, said second monomer comprises methyl methacrylate and said third monomer comprises a compound selected from the group consisting of vinyl pyrrolidone, 2-hydroxyethyl acrylate, and methacrylamide.

23. The hydrophilic polymer of claim 17 further including a cross-linking agent comprising glycidyl methacrylate.

24. The hydrophilic polymer of claim 22 wherein said molar ratio of said first monomer to said second monomer is in the range of from about 1:1 to about 10:1.

25. The hydrophilic polymer of claim 22 wherein said third monomer comprises vinyl pyrrolidone that is present in a molar ratio of 1:1 to 1.0:0.2 when compared to the total moles of first and second monomers.

26. The hydrophilic polymer of claim 22 wherein said third monomer comprises methacrylamide that is present in a molar ratio of 1:1 to 1.0:0.2 when compared to the total moles of first and second monomers.

27. The hydrophilic polymer of claim 22 wherein said third monomer comprises 2-hydroxyethyl acrylate that is present in a molar ratio of 1:1 to 1.0:0.2 when compared to the total moles of first and second monomers.

28. The hydrophilic polymer of any of claims 17 through 26 or 27 wherein said polymer when hydrated exhibits a linear expansion of from about 15 to about 25 percent.

29. A shaped article made from the hydrophilic polymer of any of claims 17 through 26 or 27.

30. A contact lens formed from the hydrophilic polymer of any of claims 17 through 26 or 27.

* * * * *